(12) United States Patent
Grillitsch et al.

(10) Patent No.: US 11,752,040 B2
(45) Date of Patent: Sep. 12, 2023

(54) WOUND CARE ARRANGEMENT AND COVERING UNIT THEREFOR

(71) Applicant: Lohmann & Rauscher GmbH, Schönau/Triesting (AT)

(72) Inventors: Peter Grillitsch, Vienna (AT); Federico Danei, Vienna (AT); Erik Steinlechner, Baden (AT); Sonja Kainz, Vienna (AT)

(73) Assignee: Lohmann & Rauscher GmbH, Schonau/Tnesting (AT)

( * ) Notice: Subject to any disclaimer, the term of this patent is extended or adjusted under 35 U.S.C. 154(b) by 972 days.

(21) Appl. No.: 16/683,982

(22) Filed: Nov. 14, 2019

(65) Prior Publication Data
US 2020/0078225 A1    Mar. 12, 2020

Related U.S. Application Data

(63) Continuation of application No. 14/382,971, filed as application No. PCT/EP2013/000636 on Mar. 5, 2013, now abandoned.

(30) Foreign Application Priority Data

Mar. 5, 2012    (EP) .................................... 12002332

(51) Int. Cl.
*A61F 13/02*     (2006.01)
*A61F 13/00*     (2006.01)
*A61M 1/00*      (2006.01)

(52) U.S. Cl.
CPC .... *A61F 13/0216* (2013.01); *A61F 13/00068* (2013.01); *A61M 1/912* (2021.05);
(Continued)

(58) Field of Classification Search
CPC ............ A61F 13/00068; A61F 13/0216; A61F 2013/00536; A61F 2013/00263;
(Continued)

(56) References Cited

U.S. PATENT DOCUMENTS 4,846,164 A    7/1989  Martz
5,425,702 A    6/1995  Carn et al.
(Continued)

FOREIGN PATENT DOCUMENTS

DE    102009019646 A1    11/2010
DE    102011106540 A1    6/2012
(Continued)

OTHER PUBLICATIONS

International Search Report dated Apr. 8, 2013 for PCT Application No. PCT/EP2013/000636 (8 pgs).
(Continued)

*Primary Examiner* — Ariana Zimbouski
(74) *Attorney, Agent, or Firm* — Schwabe, Williamson & Wyatt, P.C.

(57) ABSTRACT

The invention relates to a wound care arrangement comprising a covering unit that can be fixed on the skin surrounding a wound and that serves for producing a closed wound space comprising the wound, and a suction connection via which a vacuum can be produced in the wound space, wherein the covering unit is penneable to water vapor at least in sections.

14 Claims, 13 Drawing Sheets

(52) U.S. Cl.
CPC ... *A61M 1/962* (2021.05); *A61F 2013/00263* (2013.01); *A61M 1/964* (2021.05); *A61M 2205/7536* (2013.01)

(58) Field of Classification Search
CPC ...... A61M 1/915; A61M 1/912; A61M 1/917; A61M 1/964; A61M 1/90; A61M 27/00; A61M 2205/7536; A61M 2205/3344
See application file for complete search history.

(56) References Cited

U.S. PATENT DOCUMENTS

| | | | |
|---|---|---|---|
| 5,584,801 A | | 12/1996 | Kuroyanagi et al. |
| 7,651,484 B2 | * | 1/2010 | Heaton ............... A61M 1/95 |
| | | | 604/304 |
| 8,454,603 B2 | | 6/2013 | Webb et al. |
| 2002/0017304 A1 | * | 2/2002 | Heaton ............... A61B 46/00 |
| | | | 128/849 |
| 2005/0101940 A1 | | 5/2005 | Radl et al. |
| 2005/0137539 A1 | * | 6/2005 | Biggie ............... A61M 1/98 |
| | | | 604/313 |
| 2005/0203452 A1 | | 9/2005 | Weston et al. |
| 2005/0222527 A1 | * | 10/2005 | Miller ............... A61M 1/964 |
| | | | 602/1 |
| 2006/0149171 A1 | | 7/2006 | Vogel et al. |
| 2007/0032755 A1 | | 2/2007 | Walsh |
| 2010/0087767 A1 | | 4/2010 | McNeil |
| 2010/0179493 A1 | | 7/2010 | Heagle et al. |
| 2010/0262095 A1 | * | 10/2010 | Hall ............... A61M 1/85 |
| | | | 604/319 |
| 2010/0305524 A1 | | 12/2010 | Vess et al. |
| 2011/0112492 A1 | | 5/2011 | Bharti et al. |
| 2011/0144599 A1 | | 6/2011 | Croizat et al. |
| 2011/0178481 A1 | | 7/2011 | Locke et al. |
| 2011/0224633 A1 | * | 9/2011 | Robinson ......... A61F 13/00068 |
| | | | 604/319 |
| 2011/0257572 A1 | | 10/2011 | Locke et al. |
| 2012/0116279 A1 | | 5/2012 | Munro et al. |
| 2013/0046223 A1 | | 2/2013 | Schrammel |

FOREIGN PATENT DOCUMENTS

| | | | |
|---|---|---|---|
| DE | 102012205408 A1 | | 10/2012 |
| EP | 0620720 A1 | | 10/1994 |
| EP | 1162932 A1 | | 12/2001 |
| EP | 1088569 B1 | | 8/2003 |
| EP | 1018967 B1 | | 8/2004 |
| EP | 2495009 A1 | | 9/2012 |
| EP | 2636417 A1 | | 9/2013 |
| GB | 2265314 A | | 9/1993 |
| GB | 2329127 A | | 3/1999 |
| JP | 2009273669 | * | 11/2009 |
| WO | 2003/073970 A1 | | 9/2003 |
| WO | 2007/002835 A2 | | 1/2007 |
| WO | 2008/014358 A2 | | 1/2008 |
| WO | 2009/124548 A1 | | 10/2009 |
| WO | 2010/008167 A2 | | 1/2010 |
| WO | 2010/0011148 A1 | | 1/2010 |
| WO | 2012/083934 A1 | | 6/2012 |
| WO | 2015/022334 A1 | | 2/2015 |

OTHER PUBLICATIONS

Written Opinion dated Sep. 5, 2014 for PCT Application No. PCT/EP2013/000636 (8 pgs).
International Preliminary Report on Patentability dated Sep. 18, 2014 for PCT Application No. PCT/EP2013/000636 (10 pgs).
Non-Final Office Action dated Sep. 14, 2017 for U.S. Appl. No. 14/382,971, 6 pages.
Final Office Action dated May 2, 2018 for U.S. Application No. 14/382,971, 20 pages.
Non-Final Office Action dated Aug. 24, 2018 for U.S. Appl. No. 14/382,971, 11 pages.
Final Office Action dated May 17, 2019 for U.S. Appl. No. 14/382,971, 13 pages.

* cited by examiner

Fig. 2
a)
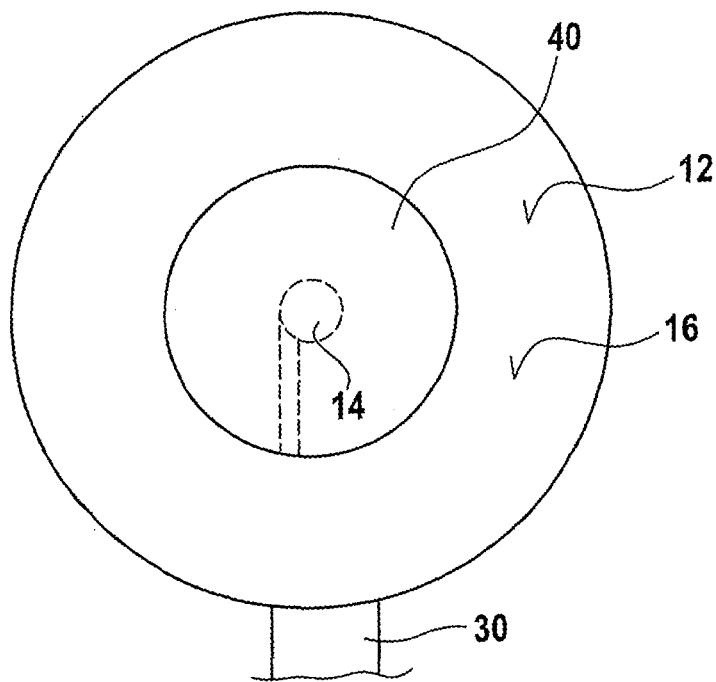
b)
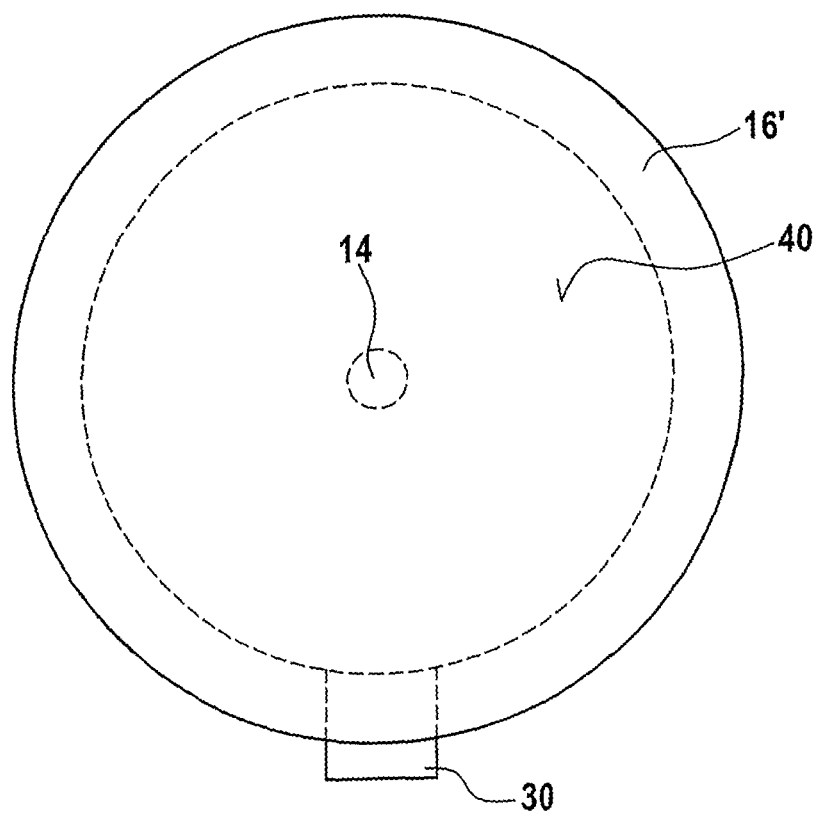

Fig. 3
a)
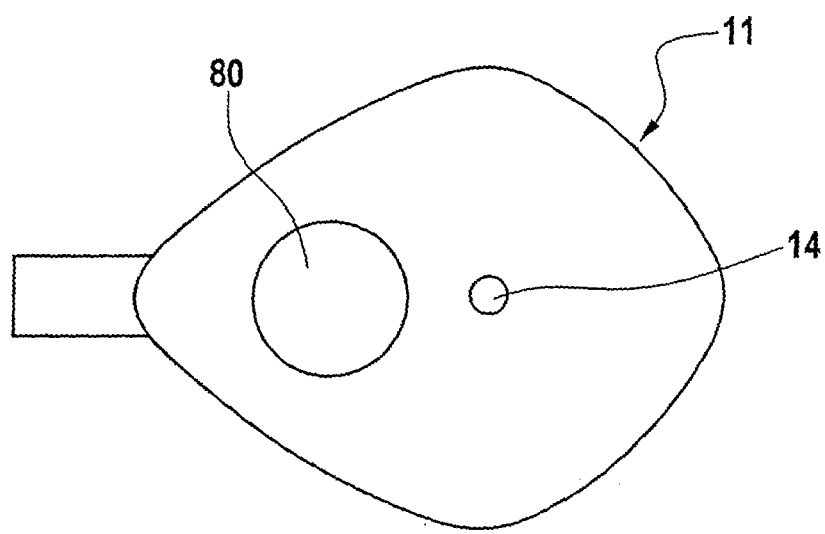
b)
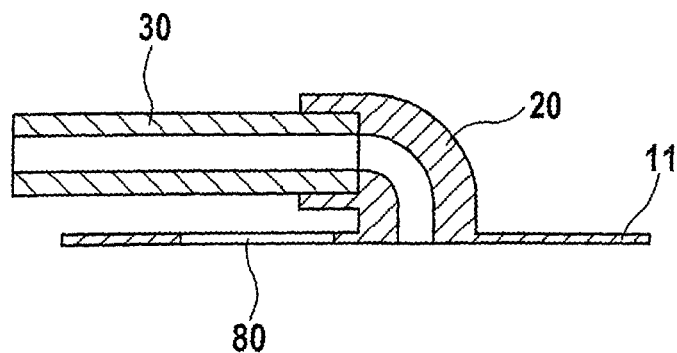

Fig. 5
a)
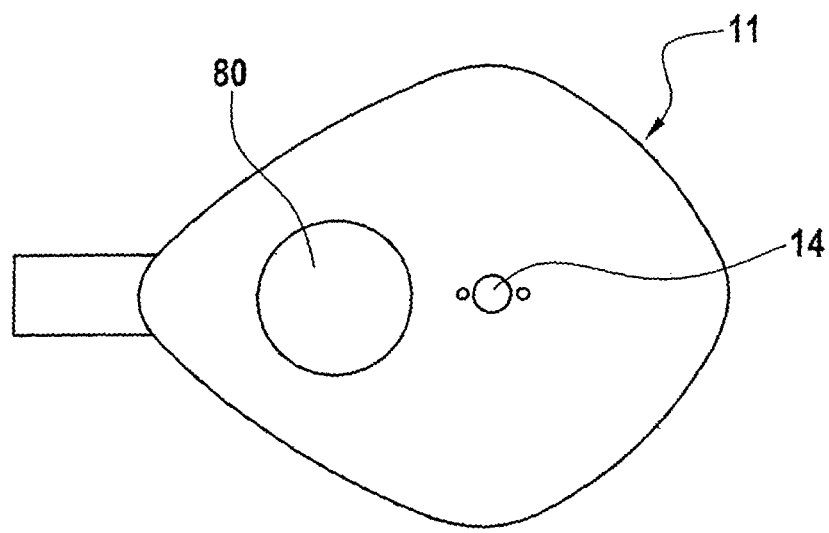
b)
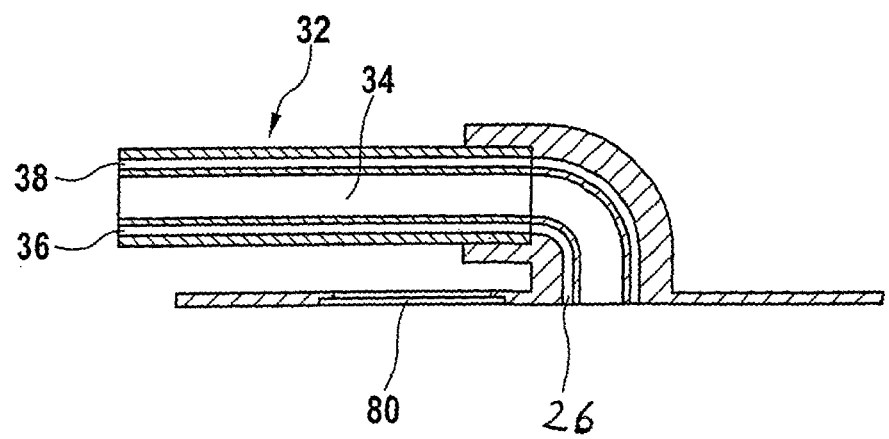

Fig. 7
a) 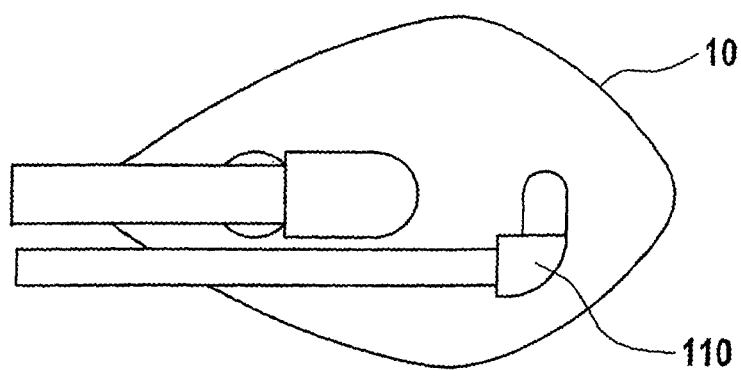
b) 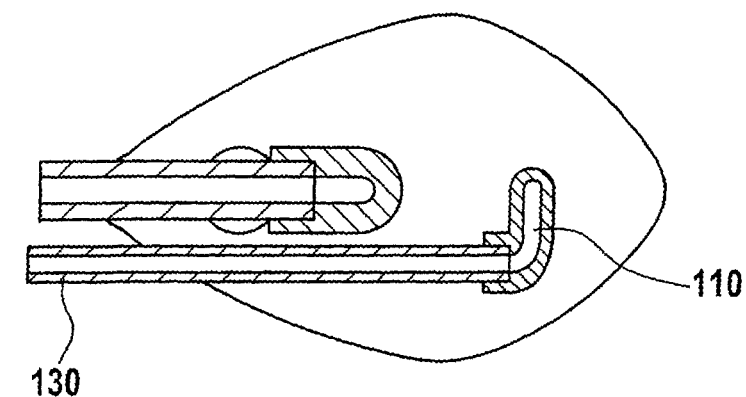
c) 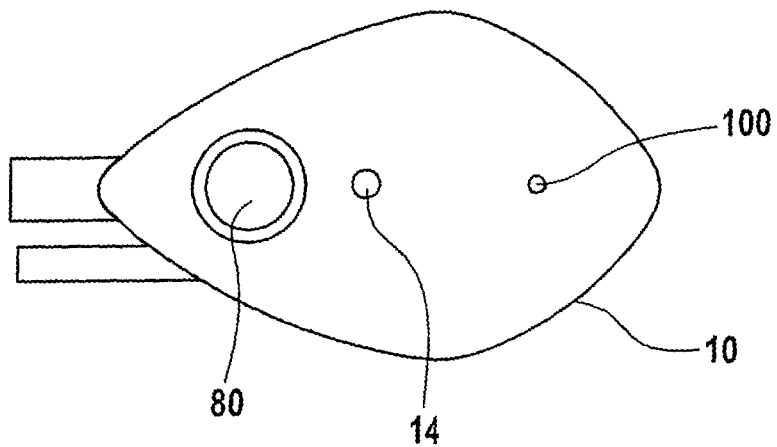

Fig. 9
a)
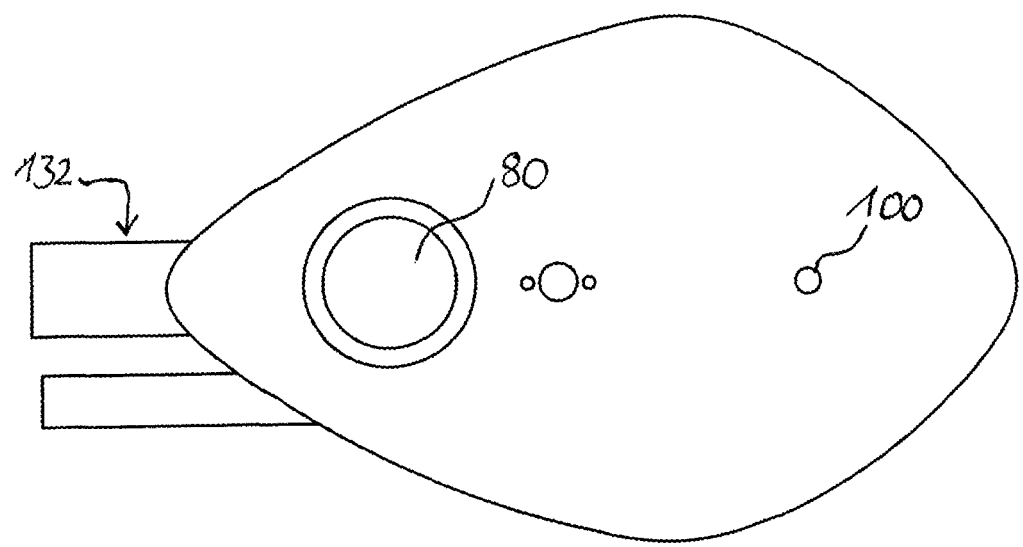
b)
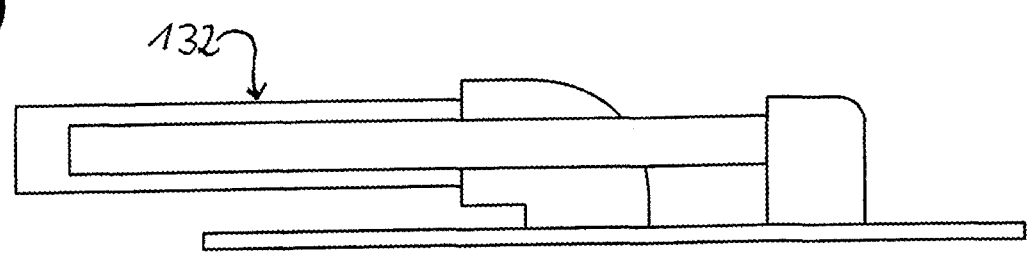
c)
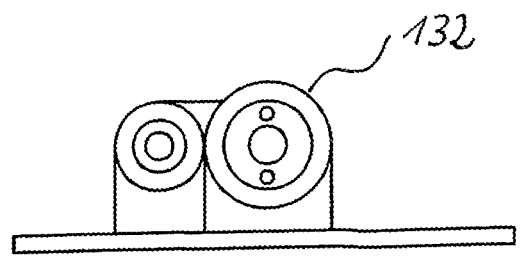

a)

b)

c)

WOUND CARE ARRANGEMENT AND COVERING UNIT THEREFOR

CROSS REFERENCE TO RELATED APPLICATION

The present application is a continuation of U.S. application Ser. No. 14/382,971, filed Sep. 4, 2014, entitled "WOUND CARE ARRANGEMENT AND COVERING UNIT THEREFORE" which is 35 U.S.C. § 371 national phase entry application of, and claims priority to, International Patent Application No. PCT/EP2013/000636, filed Mar. 5, 2013, which claims priority to European Patent Application No. EP 12002332.0, filed Mar. 5, 2012, the disclosures of which are hereby incorporated by reference in their entirety for all purposes.

BACKGROUND

The invention relates to a wound care arrangement having a covering unit that is attachable to the skin surrounding a wound and used for producing an enclosed wound space comprising the wound and a suction connection, across which a negative pressure can be generated in the wound space, as well as a covering unit for such a wound care arrangement.

Such wound care arrangements are particularly used within the scope of the so-called vacuum therapy. It has been found that, in particular, the healing of chronic wounds can be promoted by applying negative pressure to these wounds. For this purpose, it has furthermore been proven to be advantageous if the wound is covered or filled by an open-cell foam or gauze as filler material, for generating an enclosed wound space comprising the wound and, as the case may be, the filler material, is covered, and on the side of the covering unit, facing away from the wound or the filler material, a suction connection is installed, across which the wound space can be connected to a suction device designed for generating a negative pressure. In other arrangements, a flange of the suction connection is covered by the covering unit or taken up in a pocket surrounding an opening of the cover. The suction connection may, for instance, be equipped with a tube connectable, on the one hand, to a connecting device of the suction connection designed for example in the form of a tube stub and, on the other hand, to a suction device. The covering unit may, for instance, be embodied as a film-like material that is hermetically applied to the skin area adjacent to the wound.

Wound care arrangements which are usable within the scope of vacuum therapy are, for instance, described in EP 0620 720 B1. The disclosure content of this document is hereby incorporated into the specification herein by express reference with respect to the details of the foaming means and the suction device usable within the scope of the vacuum therapy. More specifically, EP 0620 720 BI recites that the invention is practiced using a negative pressure ranging from 10.1 and 100.3 kPa (0.01 to 0.99 atmospheres) and more preferably practiced using a negative pressure ranging between 50.7 and 81.1 kPa (0.5 to 0.8 atmospheres).

DE 10 2009 019 646 A1 describes a contact layer for improving the exudate management to be inserted between the filler material and the wound base and forms a drainage chamber between the filler material and the wound base. The disclosure content of this document is expressly incorporated into the specification herein with respect to the details of the contact layer or wound cover forming the drainage chamber.

Suction connections usable within the scope of vacuum therapy and connectable, via a tube, to a suction device, are, for instance, described in WO 03/073970 A1, in 2008/014358 A2 and in WO 2009/124548 A1. A suction connection, called suction head, having projections used for flow control in the area of the boundary area of the suction connection facing the wound is described in EP 1 018 967 B1. Furthermore, a suction connection having a contact surface to be applied to the filler material, in the form of a disc-like shell, is specified in EP 1 088 569 B1. In the case of a suction connection described in WO 2010/008167 A2, on the boundary area facing the filler material, channels delimited by ridges are formed that are intended for moving the wound exudate in the direction of an aspiration opening.

WO 2010/011148 A1 describes a wound care arrangement which can be used within the scope of vacuum therapy and has an impermeable tube which can be pulled over an extremity of the human body as well as a perforated body to be arranged between the wound and the tube. Using the perforated body, between the impermeable tube and the wound base, a space is created in which, via a suction connection that can be hermetically applied to the impermeable tube, a negative pressure can be generated. EP 1 162 932 B1 describes a wound care arrangement having an envelope of a plastic material and a fluid absorbing material contained in the envelope. The wound care arrangement described in this document is intended for the protection of wounds. Because it is lacking a tube connection, it is not suitable for use in vacuum therapy. In previously unpublished European patent application having the filing number 11001737.3, a wound care arrangement according to the Preamble of claim 1 is described. The disclosure content of this application is incorporated by express reference into the specification herein as far as the characteristics of the suction connection are concerned. When using conventional wound care arrangements, in many cases excessive drying out and sometimes also wound maceration are observed during vacuum therapy.

In view of these problems in the prior art, the object of the invention is based on providing a wound care arrangement, by means of which, using vacuum therapy, the healing of wounds can be reliably promoted.

According to the invention, this objective is achieved by an enhancement of the prior art wound care arrangements, being essentially characterized in that the covering unit is water vapor permeable, at least in sections.

This invention is based on the consideration that the requirements to be established as a principle for a wound cover for vacuum therapy, according to which it is necessary to create a hermetic and watertight wound space which is additionally intended to also be germ-proof, biocompatible and eudermic, is not unduly affected if, accepting impairment of the seal, the covering unit is designed permeable to water vapor. The water vapor permeability prevents, on the one hand, excessive drying out of the wound as a result of moisture being transported from the environment into the wound space, on the other hand, however, also prevents maceration of the wound by removal of excessive moisture by the cover. By using a water vapor permeable covering unit, it is possible to establish a healing promoting environment in the wound area or wound space. In addition, as a result of the water vapor permeability of the wound cover, any potential impairment of the skin surrounding the wound to which the covering unit is applied, is also reduced.

The desired adjustment of the environment in the wound space can be implemented in a particularly reliable manner, if the water vapor permeability of the covering unit, at least in sections, is 300 g/m2/24 h or more, particularly 500 g/m2/24 h, particularly preferred 750 g/m2/24 h.

In order to avoid excessive drying out of the wound, the water vapor permeability of the covering unit is expediently less than 10,000 g/m2/24 h, particularly less than 5,000 g/m2/24 h, particularly preferred 3,000 g/m2/24 h or less. The water vapor permeability data refer to measurements according to DIN EN ISO 13726-2.

If the wound is in the area of a joint, it will also be necessary to assure that the covering unit is sufficiently deformable. This can be assured if the covering unit is provided with a resilient cover film having a thickness of 0.5 μm to 200 μm, in particular 1 to 100 μm. In the interest of wound observation without removal of its wound care arrangement, it has proven to be advantageous if a transparent cover film is used. In a particularly preferred embodiment of the invention, the covering unit comprises a polyurethane polymer, particularly an aromatic polyurethane polymer.

As already explained above related to prior art wound care arrangements, it has proven to be advantageous if a filler material designed for filling the wound between the wound base and the covering unit is provided, preferably, on the suction connection side facing the filler material, a drainage layer for introducing the exudate to be aspirated from the filler material in at least one aspiration orifice of the suction connection being provided. If such a suction connection is provided, neither channel forming projections are required on the suction connection boundary area facing the filler material nor any expansion of the suction surface in the form of a disc-like shell. Rather, it is sufficient if the boundary area of the aspiration connection facing the filler material is designed flanged and plane and is penetrated by the suction opening, because the introduction of the wound exudate from the filler material is not caused by any special quality of the connection, but by the drainage layer arranged between the connection and the filler material. If the suction connection contact surface to be applied to the drainage layer is designed plane, i.e. without any projections, whether in the form of ridges delimiting channels or in the form of annular projections, as with the disc-like shells according to EP 1 088 569 B1, the impression of protruding structures into the drainage layer is prevented and, as a result, reliable functioning of the drainage layer is assured.

At this point, supplementally, it is also noteworthy that the use of water vapor permeable covering units can not only be used for creating a desired environment in the wound space, but also for minimizing stress on the skin surrounding the wound, because damage to the skin, as observed with impermeable covering units, can be ruled out.

The covering unit of a wound care arrangement according to the invention is intended to be attachable to the skin surrounding the wound. For this purpose, the covering unit per se may be equipped with an adhesive coating. The application of the covering unit according to the invention is, however, simplified if the covering unit, in the form of an uncoated, as the case may be, tubular cover film, is associated with a separate adhesive film, in particular an adhering polyurethane film, by means of which, after application to the wound, the wound covering can be attached to the skin surrounding the wound. The adhesive film may be provided in the form of a film ribbon. Within the scope of the invention, in particular, the Applicant's adhesive film offered and sold under the trade name Suprasorb F can be used as adhesive film. Related thereto, it is also noteworthy that the water vapor permeability of the covering unit is substantially affected by an adhesive coating. It may be reduced to less than one third of the uncoated covering unit.

The wound care arrangement according to the invention is particularly advantageous and suitable for the treatment of wounds on extremities, such as foot, ankle, lower leg, arm, hand. For this purpose, the covering unit may have a water vapor permeable film tube, into which this extremity can be introduced. The tubular covering unit is pulled over the extremity and, with respect to the wound, is positioned in such a way that the wound is covered and sealed by the covering unit. Subsequently, the covering unit can be attached to the skin adjacent to the wound using the adhesive film. For this purpose, the adhesive film is pulled off a reel and wound on one end of the tube in such a way that, on the one hand, it adheres to the tube and, on the other hand, to the skin.

The application of the covering unit can be simplified if one axial end of the film tube is closed, particularly hermetically, to form a stocking-like arrangement. This can be done by welding (ultrasonic, heat, RF) or by gluing (for example using a polyurethane adhesive, hot melt adhesives and/or adhesive tape). In that case, the covering unit need only be sealed on one side by an adhesive film bandage.

In the interest of simple application of the covering unit, expediently, it has a sliding friction coefficient in the range between 0.7 and 1.2, measured according to ASTM 1894-08. In this respect, sufficient stability of the covering unit can be achieved if the static friction coefficient is between 0.8 and 1.5, particularly preferred between 1 and 1.25, measured according to ASTM 1894-08. In this respect, furthermore, it has been found to be expedient if the elongation at rupture of the covering unit is more than 100%.

The application of the covering unit to the extremity bearing the wound can be further simplified if, after application to the wound, the often only very thin covering unit is provided with a support arrangement that is detachable from the wound, in particular a support film. The support film with which the covering unit may be provided, as the case may be, may be produced of transparent polyester or of a multilayer material (e.g. polyester core, bilaterally polyethylene coated) and be attached to the film-like covering unit by a lamination process. After introduction of the extremity affected by the wound into the covering unit and before sealing by adhesive film bandages, the support film must be detached, in order to assure a successful therapy process.

The suction connection of a wound care arrangement according to the invention has an aspiration orifice which faces the wound space during use and, preferably designed as a tube stub, a connecting device for establishing a connection between the aspiration orifice and an aspiration tube, the tube stub being arranged on the side of the suction connection facing away from the wound space. In this arrangement, the aspiration orifice may penetrate a flanged contact area of the suction connection, the contact area having a fastening area that preferably surrounds the aspiration orifice and preferably provided with an adhesive means, by means of which the suction connection can be glued to a boundary area of the covering unit facing away from the wound space. Alternatively the contact area may also, at least partially, be covered by the covering unit.

The film tube of a wound care arrangement according to the invention may have a prepared perforation for establishing a connection between the aspiration tube to be connected to the tube stub and the wound space. However, this complicates the application of the covering unit in a proper position in the area of the wound. For this reason, within the scope of the invention, it is particularly preferred if the film tube is completely closed in the circumferential direction and has only at least one axial opening, through which the extremity can be introduced into the tube, the perforation in the film tube associated with the aspiration orifice not being produced until after application to the wound, (and) for this purpose, the film tube can, for example, be cut open and in use, the perforation expediently surrounded by the fastening area of the suction connection.

Hereinafter, suction connections usable particularly advantageously within the scope of the invention are explained in detail.

In accordance with a particularly simple application of wound care arrangements according to the invention, it has proven to be expedient if the drainage layer to be provided, as the case may be, is attached to the contact surface, in particular glued, to the contact surface, welded, clamped and/or sewn to the contact surface. The overall arrangement, consisting of suction connection and drainage layer, can then be positioned as a whole at the desired location on the filler material or the covering unit.

As explained above related to the covering unit designed according to the invention, it has been found that during the vacuum therapy, air introduction into the wound area, continuously taking place simultaneous with the generation of negative pressure, further improves the healing process. A wound care arrangement according to a particularly preferred embodiment of the invention, therefore, has a suction connection which has, in addition to an aspiration orifice used for suctioning off the exudate, an aeration orifice arranged in particular in the flanged contact area of the suction connection and used for aeration of the wound. Continuous introduction of air into the wound area, made possible by the aeration orifice, causes a controlled and continuous pressure drop during connection of a suction device to the aspiration orifice. As a result, in particular associated with the use of a water vapor permeable covering unit, the removal of the exudate can be further improved. The pump used for suctioning off the exudate then generates a greater through-flow and an improved suction effect. It is activated more frequently and suctions off more.

For avoiding contamination of the wound, the aeration orifice is expediently associated with an antibacterial filter which may be arranged in the aeration opening or cover the aeration orifice. The filter is expediently hydrophobic and for obtaining the desired filtering action, has a pore size of 0.001 µm, in particular 0.005 µm, preferably 0.02 µm, particularly preferred 0.1 µm to 5 µm. With a pore size of less than 0.001 µm, the desired aeration is impaired. With a pore size of more than 5 µm, it is almost impossible to attain the antibacterial effect. The filter material may, in particular, contain polytetrafluoroethylene. The choice of the filter pore size also affects the air through-flow in the wound area, pore size reduction causing a reduction of the introduced air.

As an addition or an alternative to the aeration orifice, the wound care arrangement may also include, facing the aspiration orifice, a multilumen tube which may, in particular, comprise three lumens, only one of which is used for the suctioning of the exudate, another one for the controlled air supply and a third one for measuring the pressure directly at the wound. By using the multilumen tube, the suction action can be improved without causing the suction connection to need any structural modifications. The suction effect, is, however, even further improved by using an additional aeration orifice. Further enhancement is achievable if the tube stub used as connecting device has a lumen number corresponding to the multilumen tube.

In the interest of optimal wound care without removing a wound care arrangement according to the invention, it has been proven to be expedient if, in addition to the aspiration orifice, the suction connection additionally has, designed for supplying a wound care product and preferably perforating the contact area, a feed port which has, associated to it, in a particularly preferred embodiment of the invention, on the side facing away from the contact area, an additional connecting device, such as perhaps an additional tube stub, for establishing a connection between the feed port and a feed tube. Via the feel port, a rinse, as the case may be including medications, disinfectants and similar, may for example be introduced into the wound area. Like the aspiration orifice, the feed port may also be covered by the drainage layer. Within the scope of the invention, it is, however, particularly preferred if this opening is not covered by the drainage layer, in order to improve the diffusion of the rinse into the wound area.

For further enhancement of the exudate management, the wound care arrangement according to the invention may have a contact layer causing wound side drainage, arranged between the wound base and the filler material.

Within the scope of the invention, it has been found to be particularly advantageous if the drainage layer and/or the contact layer, in accordance with the wound covers according to DE 10 2009 019 646 A1, has two ribbon-like elements running approximately parallel to each other, between which a drainage chamber is formed, the depth of which in a downward direction extending approximately perpendicular to the ribbon-like elements, assures a capillary effect being exerted on the exudates taken up into the drainage chamber. For this purpose, the depth of the drainage chamber may be 5 mm or less and 0.5 mm or more. In this arrangement, each of the ribbon-like elements expediently has an opening allowing passage of body fluid into the drainage chamber, at least one opening being embodied by a channel that extends, originating from one of the ribbon-like elements, in the direction of the inner boundary area of the other ribbon-like element situated opposite and ending in the drainage chamber, its channel wall being designed in one piece with the ribbon-like element, in particular by perforation of the ribbon-like element.

In the interest of a particularly pronounced capillary action, it has proven to be advantageous if the cross-sectional area of the channel in a plane extending perpendicular to the downward direction, starting at the ribbon-like element, in the direction of the other boundary area situated opposite, is reduced, in particular for obtaining a capillary action promoting the entry of body fluid into the drainage chamber. In this arrangement, at least one ribbon-like element may comprise a plurality of openings, preferably arranged grid-like, the distance between adjacent openings being 15 mm or less, preferably 5 mm or less, particularly 3 mm or less, the mouths of the openings which are arranged in a ribbon-like element being arranged in a projection along the downward direction between the mouths of the openings arranged in the other ribbon-like element arranged in a longitudinal projection, at least one channel extending in the downward direction across 50% or more of the total depth of the drainage chamber.

The channel wall of the channels forming the opening, in an intersecting plane extending parallel to the downward direction, is designed arched, at least in sections, and continuously turns into the boundary area of the ribbon-like element. Additional characteristics of contact and/or drainage layers usable according to the invention are provided in DE 10 2009 019 646 A1, the disclosure content of which is hereby incorporated into the specification herein by express reference.

If the drainage layer only partially covers the contact surface of the suction connection, preferably covering at least the suction opening and the filter, and a fastening area surrounding the drainage layer is provided on the contact area of the suction connection, the suction connection with this fastening area can be glued to the covering unit. For this purpose, the fastening area of the suction connection can be provided with a suitable adhesive. Alternatively, instead of an adhesive, double-sided adhesive tape can be used. In this arrangement, the adhesive (for example acrylate, silicone, polyurethane) can be applied partially (e.g. in rings), in porous form or over the entire surface. The adhesive tape may also be applied partially (e.g. in rings) or over the entire surface. The double-sided adhesive tape may additionally be coated using the same adhesive on both sides (e.g. acrylate, silicone, polyurethane), or the two sides may be coated using two different adhesives (especially having silicone adhesive on the top side in contact with contact surface 12 and acrylic adhesive on the bottom.) Both adhesive and adhesive tape may be provided with a detachable protective layer.

If the drainage layer completely covers the contact area of the suction connection, the covering unit, for example designed film-like, may be glued to a fastening area of the suction connection facing away from the contact surface and surrounding the connecting device of the suction connection which is designed, for instance, in the form of a tube stub.

As in the case of prior art wound care arrangements for use in vacuum therapy, the filler material of wound care arrangements according to the invention may include open-cell foam or gauze.

As evident from the preceding explanation of wound care arrangements according to the invention, a covering unit according to the invention for use in a wound care arrangement according to the invention is essentially characterized in that it has a water vapor permeability of preferably 300 g/m2/24 h or more, being able to be embodied as polyurethane film, in particular as a film tube having dimensions adjusted to the dimensions of human extremities. The polyurethane film of a covering unit according to the invention is preferably waterproof, biocompatible, and has a thickness between 0.5 µm and 200 µm, in particular between 1 and 100 µm. The water vapor permeability is expediently less than 2000 g/m2/24 h, especially less than 1500 g/m2/24 h. The elongation at rupture of a covering unit according to the invention can be more than 100%, the static friction coefficient being between 0.8 and 1.5 and the sliding friction coefficient expediently between 0.7 and 1.2. A wound care arrangement according to the invention can be used as follows:

After applying a conventional negative pressure therapy bandage or after applying or inserting a filler material on or in the wound, a wound located on an extremity is inserted into the tubular cover film in such a way that the film covers the entire wound area and the tubular cover film projects over the edges of the wound. Taking into account its flexibility, the film is expediently dimensioned in such a way that it is seated tight and gap-free at the wound edges. The length of the tubular film can also be supplied in the form of a continuous tube and fabricated on site by cutting. The film thus covered by the filler material and the cover film is connected by its two axial ends, sealing it to the skin surrounding the wound, using customary commercial adhesive film bandages, for example under the trade name Suprasorb F from Lohmann & Rauscher GmbH. For this purpose, the film bandages are applied in such a way that they adhere to the cover film on the one hand and to the skin on the other hand. By using water vapor permeable covering units within the scope of the invention, complete sealing of the wound area by adhesive film bandages is avoided. This promotes wound healing. The cover film can be applied on a support film before and during positioning with respect to the wound. The support film must be detached after introduction of the extremity affected by the wound and before sealing by adhesive film bandages, in order to assure a successful therapy process. If the film tube used as covering unit tube is closed at one of its axial ends in the case of pre-formation of a truncated structure, for example by welding or by gluing, only one axial end of the film tube will be connected to the skin surrounding the wound, sealing it.

BRIEF DESCRIPTION OF THE DRAWINGS

Hereinafter, the invention is explained with reference to the drawing, to which express reference is made with respect to all details essential to the invention and not explicitly highlighted in the specification. Shown in the drawing:

FIG. 2 shows a suction connection of a wound care arrangement according to the invention according to a second embodiment, FIG. 3 shows a suction connection of a wound care arrangement according to the invention according to a third embodiment, FIG. 5 shows a suction connection of a wound care arrangement according to the invention according to a fourth embodiment, FIG. 7 shows a suction connection of a wound care arrangement according to the invention according to a fifth embodiment, FIG. 9 shows a suction connection of a wound care arrangement according to the invention according to a sixth embodiment.

FIG. 1a) shows a view of a suction connection 10 of a wound care arrangement according to the invention from the bottom, FIG. 1b) a view of suction connection 10 according to FIG. 1a) the top, and FIG. 1c) a sectional view of a suction connection 10 according to the invention.

DETAILED DESCRIPTION

Figure 1:
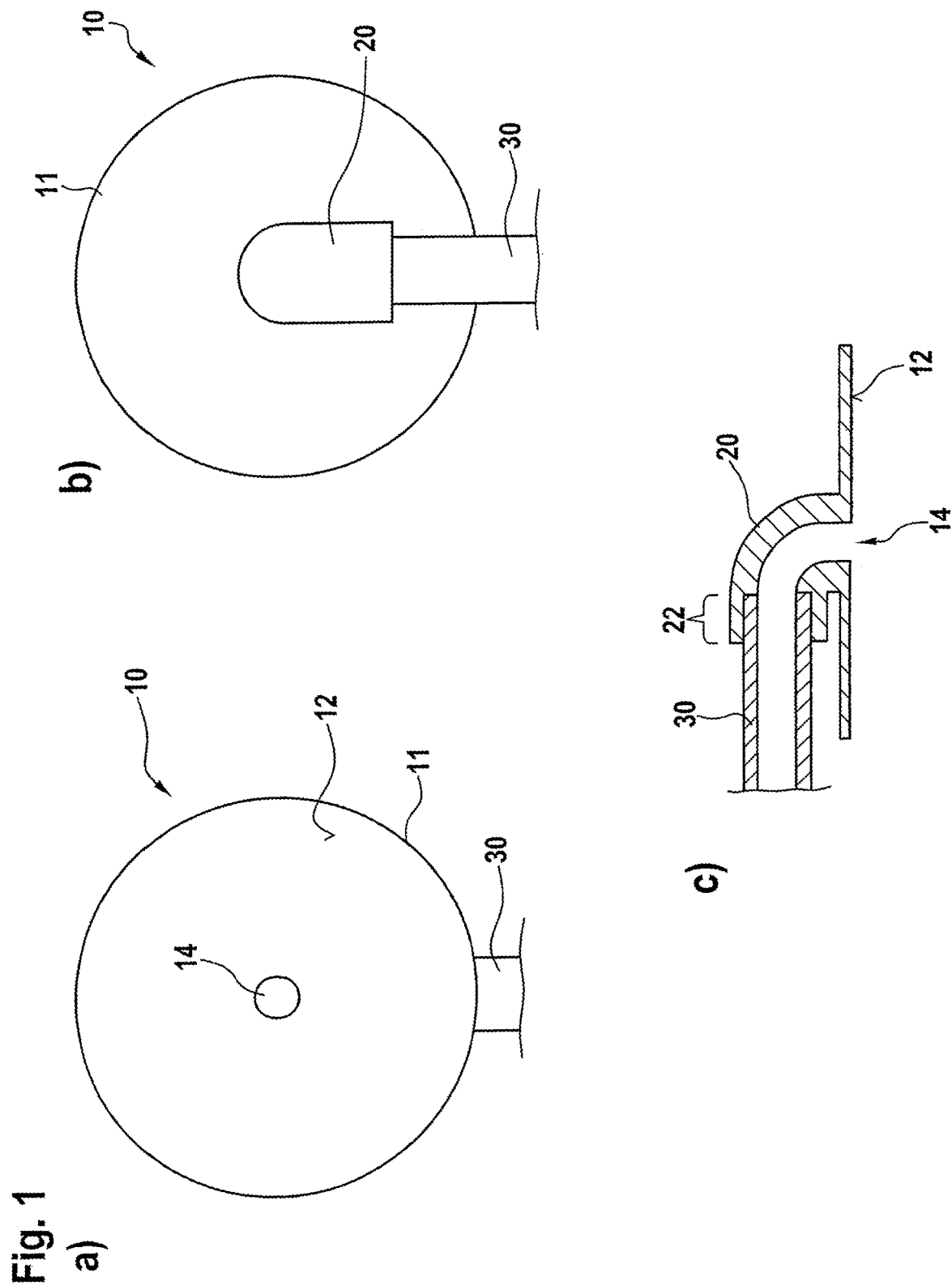
FIG. 1 shows a suction connection of a wound care arrangement according to the invention according to a first embodiment.

The suction connection 10 shown in FIG. 1 has a flanged contact area 11 with a circular disk-shaped plane contact surface 12 without any projections. Contact surface 12 is perforated by an aspiration orifice 14. In this arrangement, the likewise circular suction connection 14 is arranged in the center of contact surface 12. Aspiration orifice 14 ends in a connecting device 20, which is designed like a tube stub and causes a deflection by 90° of the exudate flow that is aligned perpendicular to contact surface 12, so that, after deflection, the flow is aligned approximately parallel to contact surface 12. Tube stub 20 has, at its end that faces away from aspiration orifice 14, a connecting area 22 with an expanded inside diameter, into which a suction tube 30 can be inserted airtight. The deflection of the aspiration flow by means of tube stub 20 causes alignment of aspiration tube 30 in a direction running parallel to contact surface 12. This allows low-interference application of suction connection 10 and aspiration tube 30 connected thereto to the body of the patient.

In the embodiment shown in FIG. 1c), aspiration tube 30 is dimensioned in such a way that its inner boundary area is aligned with an inside surface area of tube stub 20 adjacent to connection area 22 of tube stub 20, in order to minimize thereby the flow resistance for the wound exudate.

In the embodiment according to FIG. 2a), a central area of contact surface 12, comprising aspiration opening 14, is covered by a drainage layer 40 designed for the introduction of wound exudate into aspiration opening 14. Drainage layer 40 is glued to contact surface 12 and annularly surrounded by a fastening area 16 of contact surface 12.

In the embodiment according to FIG. 2b), contact surface 12 is completely covered by drainage layer 40. On the boundary area of suction connection 10 facing away from contact surface 12, surrounding tube stub 20, a fastening area 16 is provided, which, just like fastening area 16, can be provided with an adhesive layer, which can be covered by a detachable protective layer in a wound care arrangement according to the invention, before using suction connection 10.

Figure 4:
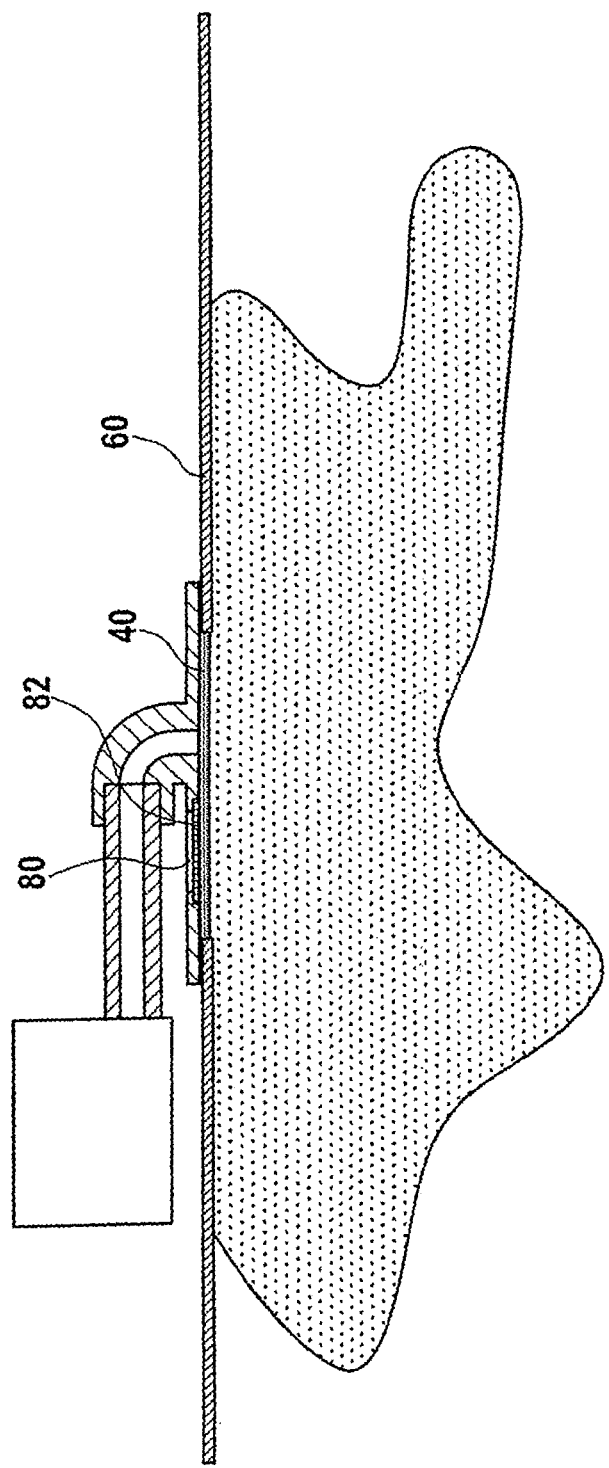
FIG. 4 shows a wound care arrangement embodied using the suction connection according to FIG. 3.

The suction connection according to FIG. 3 essentially differs from the suction connection according to FIGS. 1 and 2 in that, in addition to an aspiration orifice 14, contact area 11 also has an aeration orifice 80, by means of which the wound can be aerated in a controlled manner, in order to improve in this way the flow conditions in the wound area in the interest of improving exudate removal. Aeration orifice 80 has a greater diameter than aspiration opening 14. The edge surrounding contact area 11 may have a shoulder which, according to FIGS. 4 and 5, can be used as support surface for an antibacterial filter 82. This increases the flow resistance in the area of aeration orifice 80, which can, however, can be recompensed by adjusting the diameter of aeration orifice 80.

Within the scope of the invention, the flow resistance of filter 82 can be utilized to control the air flow. In doing so, the flow resistance is increased by reducing the filter pore size. This control enhances the generation of negative pressure with simultaneous aeration. If too large an aeration orifice 80 is selected, the negative pressure cannot be generated without using a filter. Aeration orifice 80 may also be arranged above the water vapor permeable cover film 60 (in a plan view). It is essential for the wound to be supplied with air. For this purpose, it may be expedient to provide a hole somewhat offset in cover film 60, so that the air can freely flow to aeration orifice 80.

In the embodiment shown in the drawing, the antibacterial filter 82 is made of polytetrafluoroethylene and has a pore size in the range of 0.001 μm, especially 0.005 μm, preferably 0.02 μm, particularly preferred 0.1 μm to 5 μm. In the wound care arrangement according to FIGS. 6a and 6b, it is covered by drainage layer 40. As explained with reference to FIG. 4, the suction connection according to FIG. 3 as well as the suction connection according to FIG. 1 can be attached in such a way that it is glued to a cover film 60.

Figure 6:
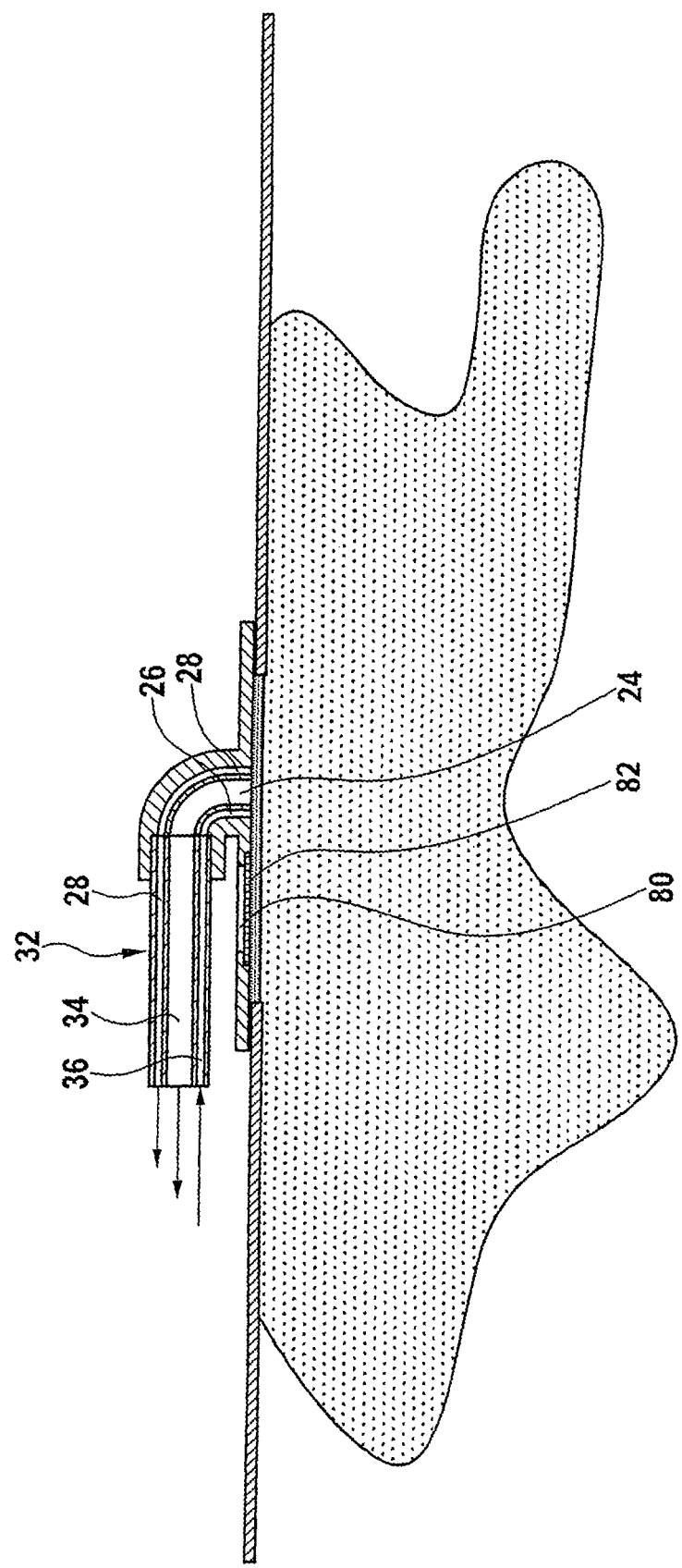
FIG. 6 shows a wound care arrangement having a suction connection according to FIG. 5.

The embodiment according to FIG. 5 essentially differs from the embodiment according to FIG. 3 in that the aspiration tube is implemented as a three-lumen tube 32 and, as schematically indicated in FIG. 6, the middle and largest lumen 34 is used for generating the negative pressure in the wound area, a small lumen 36 can be used for aerating the wound, and an additional smaller lumen 38 is intended for measuring the pressure in the wound area. Connection area 22 also comprises lumens 24, 26 and 28 corresponding to the lumens 32, 34 and 36.

The embodiment according to FIGS. 5 and 6 additionally comprises, in addition to aeration lumen 26, an aeration orifice 80, in order to allow further improving the exudate management.

The embodiment according to FIG. 7 essentially differs from the embodiment according to FIG. 3 in that, in addition to the aspiration opening 14 and the aeration orifice 80, additionally a feed port 100 into contact area 11 of suction connection 10 is provided, which is associated with another tube stub 110 for connecting feed port 100 to another tube 130. Via tube 130, the additional tube stub 110 and feed port 100, wound care agents, such as a rinse, as the case may be, mixed with medications, disinfectants or the like, can be introduced into the wound area. The embodiment according to FIG. 7 can be used even without using a separate aeration orifice 80 because feed port 100 can also be used for aeration. For the purpose of good exudate management, it has, however, proven to be particularly expedient if, in addition to aspiration opening 14, both an aeration orifice 80 and a feed port 100 are provided in contact area 11 of suction connection 10.

Figure 8:
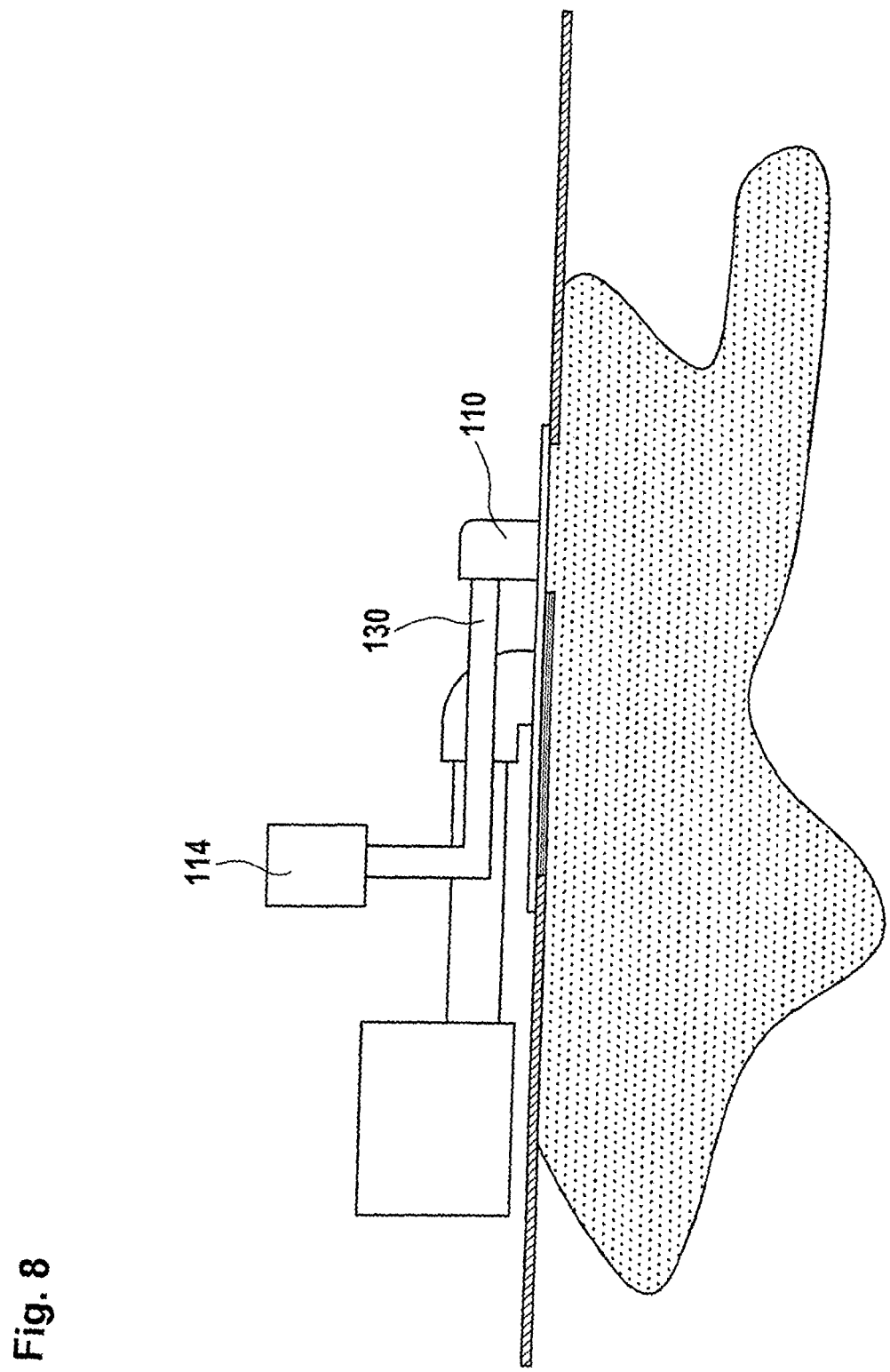
FIG. 8 shows a wound care arrangement having a suction connection according to FIG. 7.

As evident from FIG. 8, the rinse can be introduced into the area of the wound via the additional tube 130 and the additional tube stub 110 using an appropriate metering element 114. For this purpose, it has proven to be particularly expedient if the feed port 100 is not covered by drainage layer 40, in order to assure thereby the removal by aspiration of wound exudate without being affected by the supplied rinse and in order to prevent the supplied rinse from being immediately removed again by aspiration.

The embodiment according to FIG. 9 differs from the embodiment explained with reference to FIG. 7 in that a three-lumen tube 132 is used, the design and functioning of which are comparable to the design according to FIG. 5. For this purpose, the design according to FIG. 9 has a three-lumen tube for removal for removal by aspiration of wound exudate, aeration of the wound area and an aeration orifice 80 pressure measurement as well as a feed port 100. This allows assuring optimal wound management.

The embodiments explained with reference to FIGS. 3 to 9 have, in contrast to the embodiments explained with reference to FIGS. 1 and 2, a contact area of a shape that differs from circular, being approximately rhombic in shape. The corners of the rhombs are rounded. The rhombic shape provides a longitudinal axis, which allows the arrangement of aspiration orifice, aeration orifice and feed port in a line.

Figure 10:
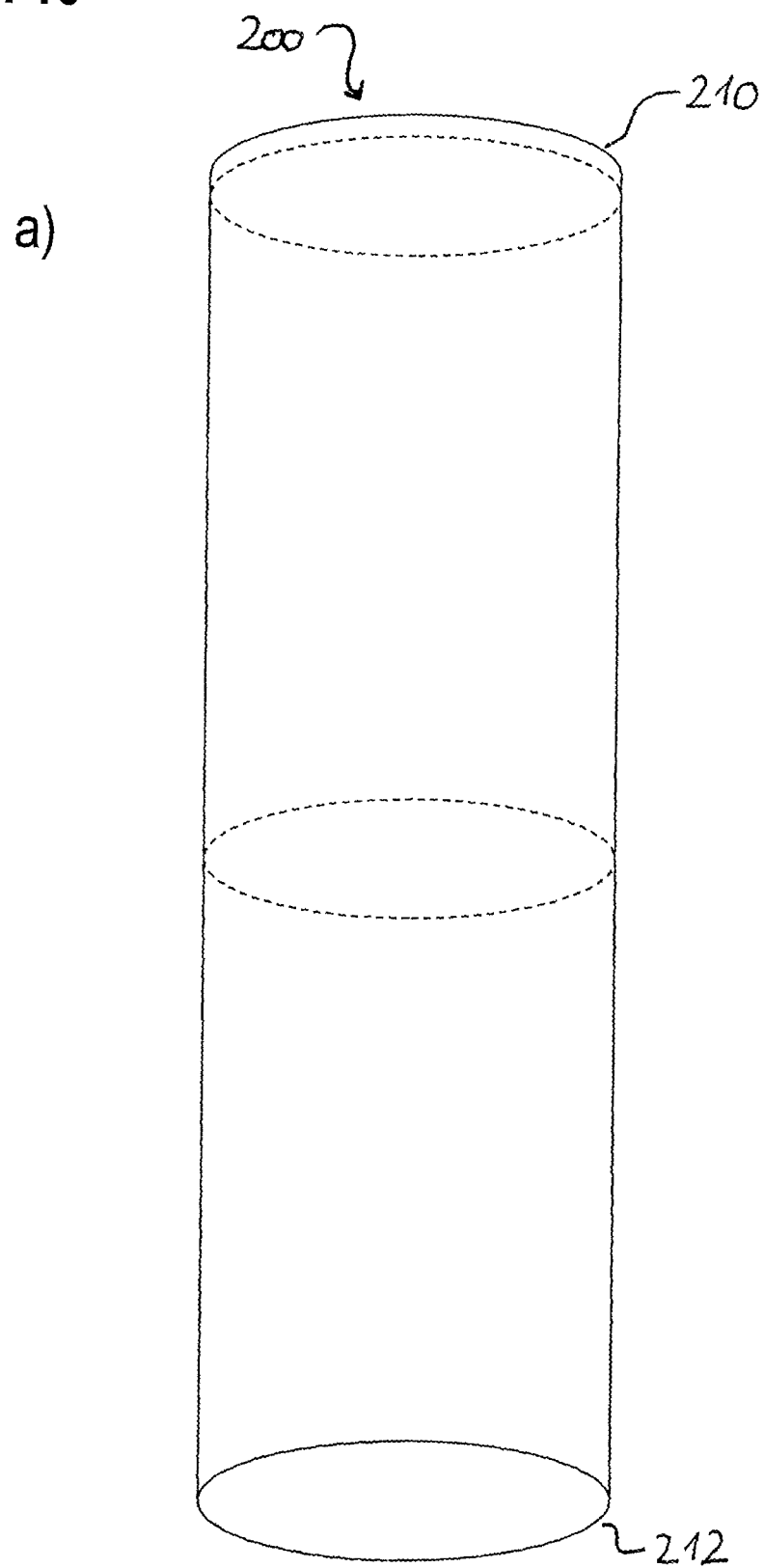
FIG. 10 shows embodiments of covering units according to the invention for wound care arrangements according to the invention.
Figure 10:
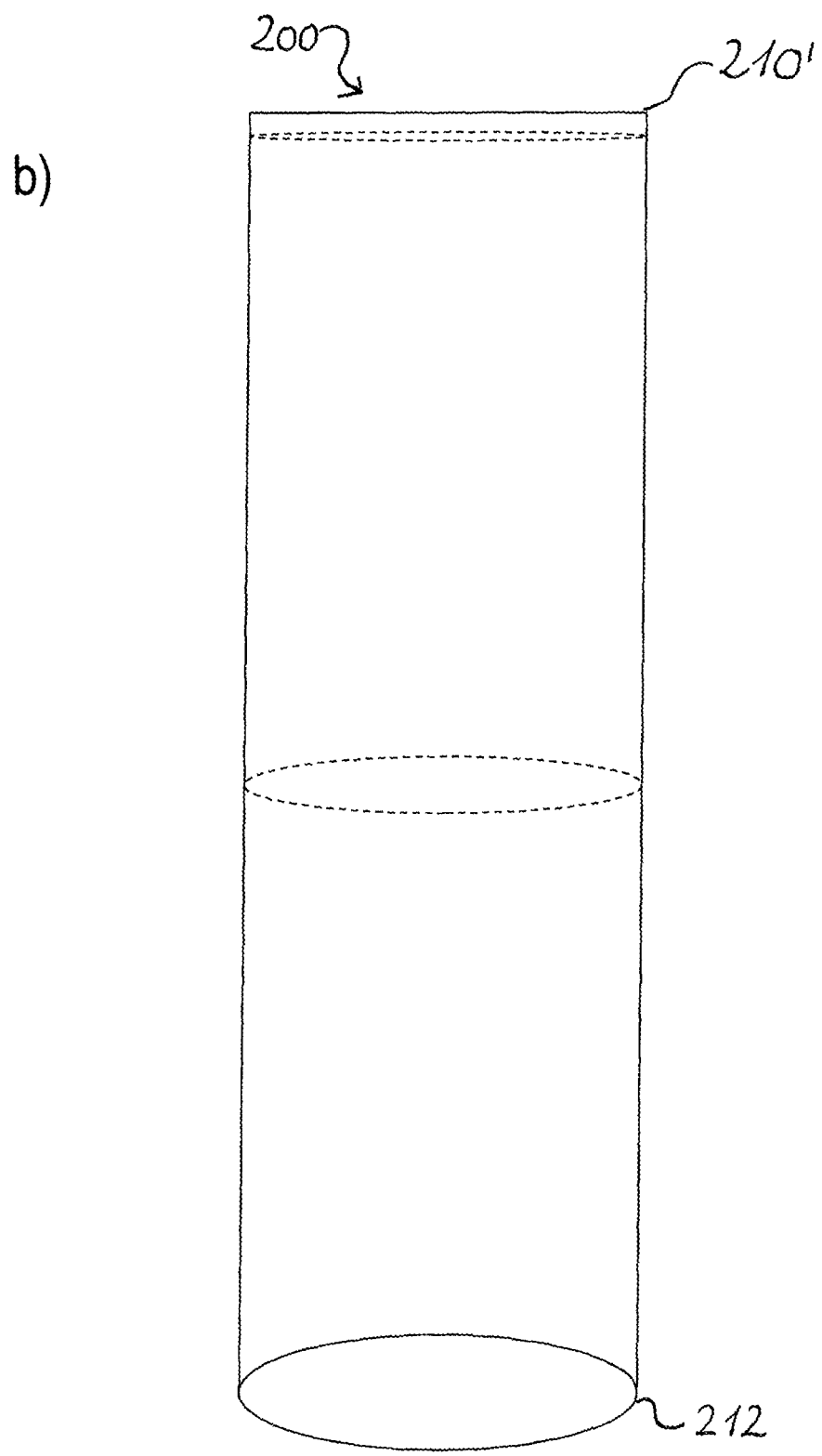
Figure 10:
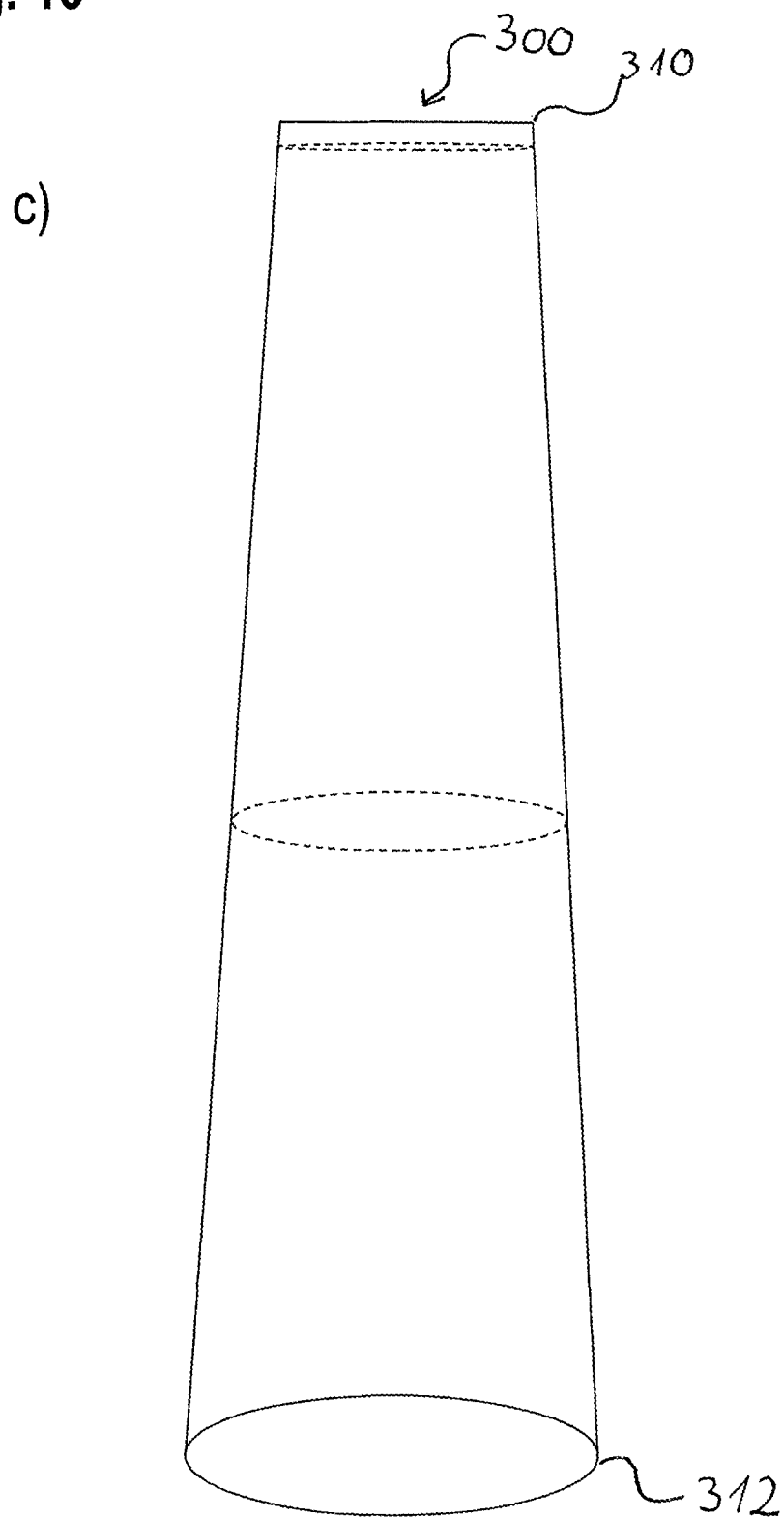

The covering unit illustrated in FIG. 10a) is embodied as a film tube 200, which may take on circular cylinder jacket shape. The two ends 210 and 212 of the film tube shown in FIG. 10-a) are designed open in such a way that the tube as a whole can be pulled over one extremity. The covering unit according to the invention according to FIG. 10b) essentially differs from the covering unit according to FIG. 10a) in that the upper end 210' of the hollow tube 200 is closed.

In the embodiment according to FIG. 10c), the covering unit embodied as film tube is spreadable as a truncated in the form of a cone jacket, i.e. tapered. In this arrangement, one end, such as upper end 310, may be closed, while the other one, such as the lower end 312, may be designed to be open. Particularly preferred, the end having the smaller cross-section will be closed. In that case, the film tube can be slipped over a foot somewhat like a stocking or, as the case may be, over a hand, like a glove.

Figure 11:
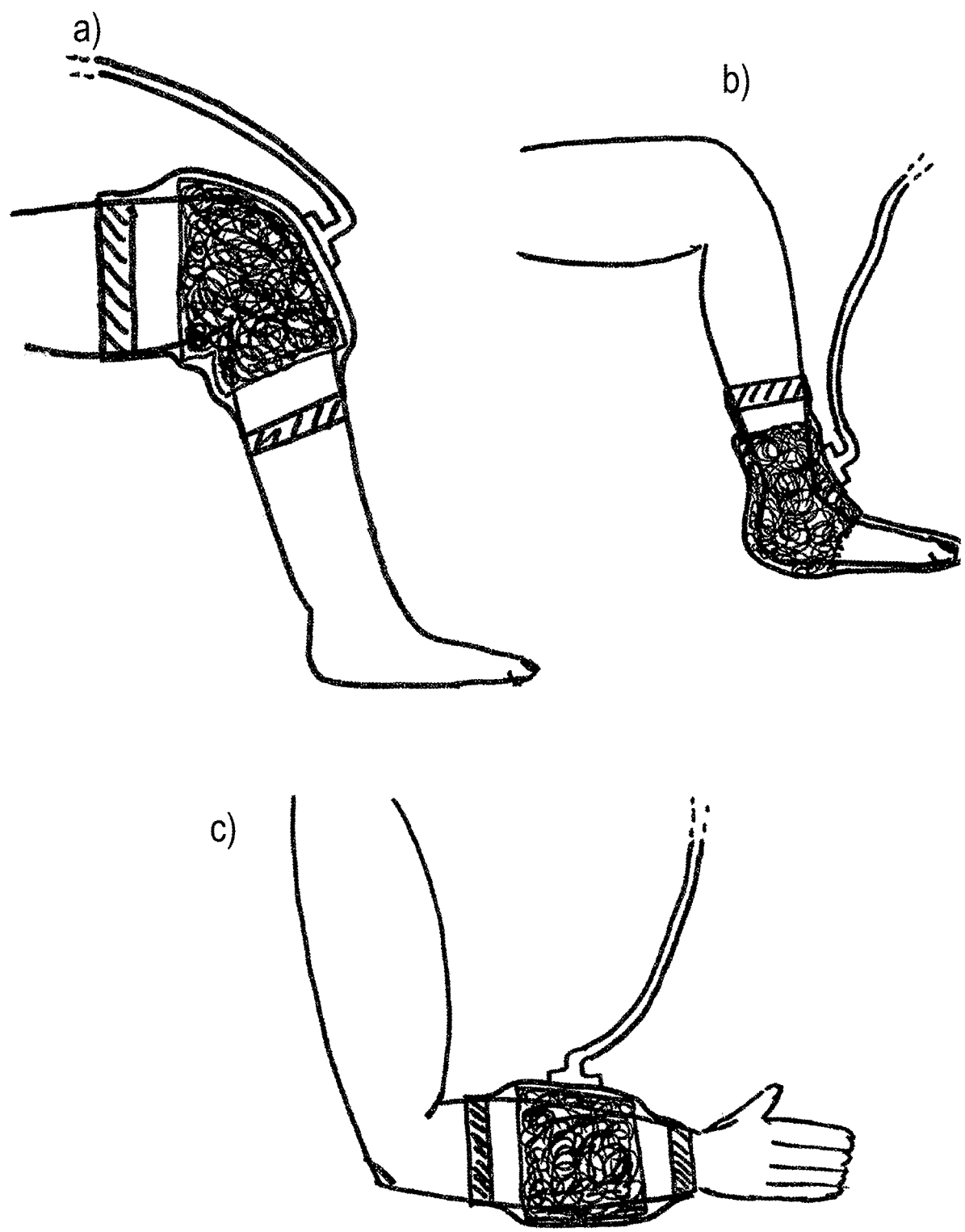
FIG. 11 shows exemplary embodiments of wound care arrangements according to the invention.

In FIG. 11. various exemplary embodiments of wound care arrangements according to the invention are illustrated. In this case, FIG. 11a) shows the application in the area of the knee joint. It can be seen that the covering unit in analogy to the covering unit shown in FIG. 10c) or 10a) is designed tubular and open at both ends and is attached to the surrounding skin by the ends opposite each other using adhesives means.

In the exemplary embodiment according to FIG. 11b), the wound care arrangement is applied to an ankle. In this example, the cover unit is embodied like a closed film tube, which is attached to the surrounding skin in the area of the user's calf.

Finally, in the exemplary embodiment shown in FIG. 11c), the wound care arrangement is applied to the forearm of a patient. In this example, the covering unit is designed as a film tube open at both ends, the film tube being designed tapered according to the illustration in FIG. 10c) and attached to the surrounding skin by the two opposite edges.

The invention shall not be limited to the embodiments explained with reference to the drawing. In particular, the use of tubular cover film is intended, which may even, if appropriate, be mounted to support film, the support film being detachable from the cover film after application of the cover film to the wound. For this purpose, expediently, in the peripheral direction, completely closed film tubes will be used, which only have, at least on one axial end, an opening, the opening in the film tube required for drainage of the exudate via the suction connection being formed after application of the film tube to the wound. For this purpose, the film tube may for example be cut open at the appropriate location. Besides polyurethane film, other skin-compatible and water vapor permeable film can be used. It is essential that the covering unit delimits the enclosed wound space substantially airtight and waterproof, is germ-proof, has appropriate water vapor permeability, is biocompatible and eudermic as well as cuttable and, if necessary, can be easily applied using additional support film.

The invention claimed is:

1. Wound care arrangement, comprising:
    a covering unit that comprises a film tube into which a human extremity is to be introduced to provide an enclosed wound space associated with a wound in the human extremity, wherein the covering unit is water-vapor permeable, at least in sections; and
    a suction connection coupled with the covering unit, to provide for a generation of a negative pressure in the wound space, wherein the suction connection includes:
        a contact area to provide contact between the wound space and the covering unit;
        an aspiration orifice disposed in the contact area, to provide suction within the wound space; and
        an aeration orifice disposed in the contact area to provide aeration of the wound space, wherein a diameter of the aeration orifice is greater than a diameter of the aspiration orifice.

2. The wound care arrangement of claim 1, wherein one or more corners of the contact area have rounded shapes.

3. The wound care arrangement of claim 1, further comprising:
    an anti-bacterial filter to cover the aeration orifice.

4. The wound care arrangement according to claim 3, wherein the aeration orifice includes an edge surrounding the aeration orifice, wherein the edge has a shoulder to be used as support surface for the anti-bacterial filter.

5. The wound care arrangement of claim 1, further comprising:
    a tube stub coupled with the aspiration orifice in the contact area; and
    a suction tube coupled with the tube stub, to further provide the suction within the wound space.

6. The wound care arrangement of claim 5, wherein the tube stub has a substantially direct-angled shape, to provide a parallel alignment between the suction tube and the contact area.

7. The wound care arrangement of claim 5, wherein the suction tube comprises a multi-lumen tube having at least first and second lumens.

8. The wound care arrangement of claim 7, wherein the first lumen is to provide a negative pressure within the wound space, wherein the second lumen is to provide aeration of the wound space.

9. The wound care arrangement of claim 7, wherein the multi-lumen tube further includes a third lumen to provide a measurement of the negative pressure in the enclosed wound space.

10. The wound care arrangement of claim 7, wherein the tube stub comprises first and second lumens that correspond to the first and second lumens of the multi-lumen tube.

11. The wound care arrangement of claim 1, further comprising:
    a feed port disposed in the contact area along the longitudinal axis of the contact area.

12. The wound care arrangement of claim 11, further comprising:
    a feed port tube stub coupled with the feed port; and
    a feed tube, coupled with the feed port stub, to provide feeding connection for the feed port.

13. The wound care arrangement of claim 1, wherein the aspiration orifice is disposed along a longitudinal axis of the contact area.

14. The wound care arrangement of claim 13, wherein aeration orifice is disposed along the longitudinal axis of the contact area.

* * * * *

UNITED STATES PATENT AND TRADEMARK OFFICE
CERTIFICATE OF CORRECTION

PATENT NO. : 11,752,040 B2
APPLICATION NO. : 16/683982
DATED : September 12, 2023
INVENTOR(S) : Peter Grillitsch et al.

It is certified that error appears in the above-identified patent and that said Letters Patent is hereby corrected as shown below:

In the Claims

Column 12
Lines 53-54 "...wherein aeration orifice..." should read -- wherein the aeration orifice --

Signed and Sealed this
Twenty-first Day of May, 2024

Katherine Kelly Vidal
*Director of the United States Patent and Trademark Office*